United States Patent [19]
Ancillotti et al.

[11] 3,979,461
[45] Sept. 7, 1976

[54] PROCESS FOR THE PREPARATION OF METHYL TERT-BUTYL ETHER

[75] Inventors: Francesco Ancillotti, San Donato Milanese; Gianni Oriani; Ermanno Pescarollo, both of Milan, all of Italy

[73] Assignee: Sham Progetti S.p.A., San Donato Milanese, Italy

[22] Filed: May 21, 1975

[21] Appl. No.: 579,692

[30] Foreign Application Priority Data

May 21, 1974 Italy................................. 23009/74

[52] U.S. Cl.......................... 260/614 A; 260/666 R; 260/677 A
[51] Int. Cl.².................... C07C 41/06; C07C 41/10
[58] Field of Search......................... 260/614 A, 616

[56] References Cited
UNITED STATES PATENTS

| | | | |
|---|---|---|---|
| 1,968,601 | 7/1934 | Edlund et al. | 260/614 A X |
| 2,480,940 | 9/1949 | Leam et al. | 260/614 A |
| 3,119,766 | 1/1964 | Voltz et al. | 260/614 A X |
| 3,846,088 | 11/1974 | Brown et al. | 260/614 A X |

FOREIGN PATENTS OR APPLICATIONS

| | | | |
|---|---|---|---|
| 957,000 | 4/1964 | United Kingdom | 260/614 A |
| 1,176,620 | 1/1970 | United Kingdom | 260/614 A |

*Primary Examiner*—Howard T. Mars
*Attorney, Agent, or Firm*—Ralph M. Watson

[57] ABSTRACT

Methyl tert-butyl ether is prepared, and a stream of hydrocarbons containing isobutylene is freed therefrom, by reacting the isobutylene with methanol in a two stage process wherein, in the first stage, a stream of hydrocarbons containing isobutylene and methanol is fed to a primary reaction zone where the isobutylene and methanol partially react in the temperature range of from 50° to 90°C and at a pressure of from 10 to 30 atmospheres in the presence of a catalyst to form methyl tert-butyl ether which is separated by distillation from the residue of isobutylene and methanol and all other hydrocarbons in the feed stream, and, in a second stage, the residue of isobutylene and methanol and other hydrocarbons is fed to a secondary reaction zone where the residue of isobutylene and methanol react in the vapor phase, at a temperature in the range of 60° to 100°C and a pressure of from 15 to 40 atmospheres in the presence of a catalyst consisting of an acid ion exchange resin, to form the balance of methyl tert-butyl ether which is recovered by distillation to leave a balance of other hydrocarbons practically free from isobutylene.

2 Claims, 1 Drawing Figure

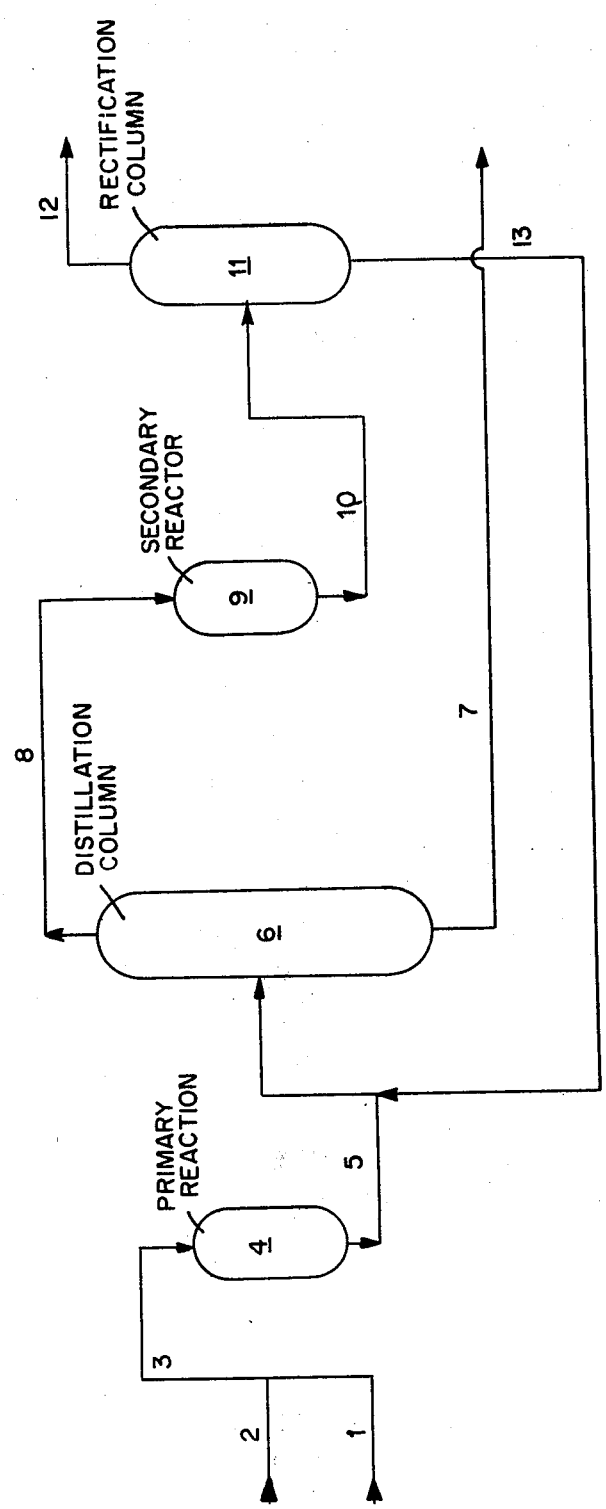

PROCESS FOR THE PREPARATION OF METHYL TERT-BUTYL ETHER

The present invention relates to a process for the preparation of tert-alkyl ethers.

It is known that tert-alkyl ethers can be prepared by reacting a primary alcohol with an olefine having a double bond on a tertiary carbon atom; thus methanol reacts with isobutylene and isoamylenes (2 methyl pentene 1 or 2 methyl pentene 2) to form respectively methyl tert-butyl ether (MTBE) and methyl tert-amyl ether (MTAE).

The reaction is selective for tertiary olefines so that it constitutes a valid process for their removal from olefinic streams in which they are contained together with linear unreactive olefines.

The reaction has an equilibrium which is the more favorable to the synthesis of the ether the lower the reaction temperature in accordance with its negative enthalpy.

It is known that the reaction is catalyzed by Lewis acids (aluminium trichloride, boron trifluoride), mineral acids (sulphoric acid) and organic acids (alkyl and aryl sulphonic acids, ion exchange resins).

Particularly suitable for the task are ion exchange resins in their acid form and it is known that the best results are obtained by means of macroreticular resins of the type "Amberlyst 15".

By means of such last named catalysts it is possible to reach thermodynamic equilibrium within industrially acceptable contact times in the temperature range of 50-60°C.

At lower temperatures, thermodynamically more favourable, the kinetics are not sufficiently favorable to permit reaching equilibrium in practice.

This fact limits conversions.

Obviously the conversion of a reagent can be increased by increasing in the feed the content of the other reagent but this involves a lowering of the conversion of the excess reagent.

This can cause same drawbacks, as for instance in the synthesis of MTBE starting from methanol and isobutylene contained in an olefinic stream; the use of excess isobutylene involves the fact that the olefinic stream after separation of MTBE still contains 5-10% isobutylene and this constitutes a drawback when such stream has to be utilized for the production of maleic anhydride or butadiene; on the other hand an excess of methanol renders the purification of MTBE very expensive because of the formation of azeotropes. It has been surprisingly found that it is possible to increase conversion simply by carrying out the reaction process in two stages (reactor and post reactor). The subject of the present invention is a process for the preparation of tert-alkyl ethers which involves feeding a hydrocarbon stream containing the olefin (having a double bond on the tertiary carbon atom) together with the primary alcohol to a primary reaction zone (primary reactor) at a temperature in the range of from 50° to 90°C and a pressure range of 10-30 atmospheres, separating the produced ether from the hydrocarbon stream and residual alcohol by distillation, feeding the hydrocarbon stream still containing the tertiary olefin and residual alcohol to a secondary reaction zone (post-reactor) wherein the reaction is carried out in the liquid phase at a temperature in the range of from 60° to 100°C, a pressure range of 15-40 atmospheres in the presence of an acid macroreticular resin as catalyst. The produced ether is subsequently removed by distillation.

Besides obtaining the desired ether with very high conversions the process which is the subject of the present invention makes it possible to lower the amount of olefine with a double bond on the tertiary carbon atom to levels lower than 2%. Such a result is attainable also when the olefin with a double bond on the tertiary carbon atom is in excess with respect to the stoichiometric value in the feed to the second reaction stage because of the formation of dimers or polymers of the olefine.

BRIEF DESCRIPTION OF THE DRAWING

The drawing is a schematic illustration of a preferred process for carrying out our invention;

With reference to the accompanying drawing, the process which is the subject of the present invention will now be illustrated for the particular case of the preparation of MTBE, even though, as noted above, the process is valid for the preparation of other ter-alkyl ethers, the drawing being intendend as not restrictive of the invention itself.

A C4 olefinic stream 1 containing isobutene is fed together with methanol 2 through 3 to the primary reactor 4.

In the primary reactor 4 isobutene is partially transformed into methyl tert-butyl ether. The mixture leaving reactor 4 through 5 is fed to distillation column 6 from the bottom of which methyl tert-butyl ether is discharged through 7.

From the top of column 6 an olefinic stream 8 free from MTBE is discharged, said stream being forwarded to secondary reactor 9 wherein in the liquid phase at a temperature in the range of from 60° to 100°C and in presence of Amberlyst 15 as catalyst the remaining portion of isobutene is transformed into MTBE.

The hydrocarbon stream leaving the secondary reactor 9 is then forwarded through 10 to rectification in a column 11 in order to separate all butenes which are discharged as overhead products through 12 and MTBE which is discharged as bottom product through 13 is recycled to the distillation column 6.

The quantity of isobutylene in the C$_4$ olefinic stream is reduced to values lower than 2%. Also by working with an excess of isobutylene in the feed to the secondary reactor said quantity of isobutylene is reduced to values lower than 2% by dimerization of isobutylene. Together with isobutylene dimerization there is also a sensible isomerization of C$_4$ linear olefins which tends to approach the thermodynamic equilibrium.

As a matter of fact in the case of the reaction of isobutene and methanol, used at equimolecular ratios, there are total conversions not lower than 98%. We shall now give some numerical example for the purpose of better illustrating the invention without limiting the same.

EXAMPLE 1

An olefinic stream having the following composition:

| | |
|---|---|
| isobutene | 50.00% by weight |
| butene 1 | 28.50% by weight |
| butene 2 trans | 8.02% by weight |
| butene 2 cis | 0.03% by weight |

| | |
|---|---|
| other C₄ hydrocarbons | 13.18% by weight | was mixed with methanol so as to have a isobutene/methanol molar ratio = 1.0 and was fed with LHSV = 5 to the primary reactor containing Amberlyst 15 wherein it reacted at the temperature of 60°C and pressure of 15 atmospheres. The stream leaving the primary reactor had the following composition:

| | |
|---|---|
| MTBE | 57.59% by weight |
| methanol | 1.32% by weight |
| isobutene | 2.22% by weight |
| butene 1 | 22.16% by weight |
| butene 2 trans | 6.23% by weight |
| butene 2 cis | 0.23% by weight |
| other C₄ hydrocarbons | 10.25% by weight | was fed to the distillation column obtaining as bottom product MTBE at 98% purity and as overhead product a stream having the following composition:

| | |
|---|---|
| MTBE | 0.25% by weight |
| methanol | 1.89% by weight |
| isobutene | 5.23% by weight |
| butene 1 | 52.81% by weight |
| butene 2 trans | 14.86% by weight |
| butene 2 cis | 0.56% by weight |
| other C₄ hydrocarbons | 24.40% by weight | wherein the isobutene/methanol molar-ratio was 1.57 and wherein there were the following ratios between the linear olefines:

| | | |
|---|---|---|
| butene 1/butene 2 trans | = | 3.55 |
| butene 1/butene 2 cis | = | 94.30 |

Said stream was reacted in the secondary reactor in presence of Amberlyst 15 at LHSV equal to 5 and a temperature of 60°C forming a product whose composition was the following:

| | |
|---|---|
| MTBE | 5.15% by weight |
| methanol | traces |
| isobutene | 1.97% by weight |
| butene 1 | 50.70% by weight |
| butene 2 trans | 15.24% by weight |
| butene 2 cis | 1.41% by weight |
| other C₄ Hydrocarbons | 24.68% by weight |
| C₈ olefines | 0.80% by weight | and in which the ratio between the linear olefines was the following

| | | |
|---|---|---|
| Butene 1/Butene 2 trans | = | 3.32 |
| Butene 1/Butene 2 cis | = | 35.94 |

EXAMPLE 2

A stream fed to the secondary reactor having the same characteristics as those of the stream used in example 1 was reacted on Amberlyst 15 at a LHSV of 5 and a temperature of 80°C forming a product having the following composition:

| | |
|---|---|
| MTBE | 5.15% by weight |
| methanol | traces |
| isobutene | 1.15% by weight |
| butene 1 | 45.37% by weight |
| butene 2 trans | 16.28% by weight |
| butene 2 cis | 4.00% by weight |
| other C₄ hydrocarbons | 24.18% by weight |
| C₈ olefines | 3.87% by weight | and in which the ratio between the linear olefines was the following:

| | | |
|---|---|---|
| Butene 1/Butene 2 trans | = | 2.79 |
| Butene 1/Butene 2 cis | = | 11.34 |

EXAMPLE 3

A stream to the secondary reactor having the same characteristics as those of the streams used in examples 1 and 2 was reacted on Amberlyst 15 at a LHSV of 5 and at a temperature of 90°C forming a product having the following composition:

| | |
|---|---|
| MTBE | 5.15% by weight |
| methanol | traces |
| isobutene | 0.70% by weight |
| butene 1 | 30.72% by weight |
| butene 2 trans | 21.69% by weight |
| butene 2 cis | 11.10% by weight |
| other C₄ hydrocarbons | 23.84% by weight |
| C₈ olefins | 6.80% by weight | and in which the ratio between the linear olefins was the following:

| | | |
|---|---|---|
| Butene 1/Butene 2 trans | = | 1.42 |
| Butene 1/Butene 2 cis | = | 2.77 |

EXAMPLE 4

A stream to the secondary reactor having the same characteristics as those of the streams utilized in the foregoing examples was reacted on Amberlyst 15 at a LHSV of 15 and at a temperature of 90°C forming a product having the following composition:

| | |
|---|---|
| MTBE | 5.15% by weight |
| methanol | traces |
| isobutene | 1.80% by weight |
| butene 1 | 47.33% by weight |
| butene 2 trans | 15.82% by weight |
| butene 2 cis | 3.23% by weight |
| other C₄ hydrocarbons | 24.37% by weight |
| C₈ olefins | 2.30% by weight | and in which the ratio between the linear olefines was the following:

| | | |
|---|---|---|
| Butene 1/Butene 2 trans | = | 3.00 |
| Butene 1/Butene 2 cis | = | 14.65 |

EXAMPLE 5

A stream to the secondary reactor different from the foregoing ones having as composition:

| | |
|---|---|
| Methanol | 2.40% by weight |
| isobutene | 4.20% by weight |
| butene 1 | 53.25% by weight |
| butene 2 trans | 14.98% by weight |
| butene 2 cis | 0.56% by weight |
| other $C_4$ hydrocarbons | 24.60% by weight | wherein the molar ratio between isobutene and methanol was 1 and having the following ratio between the linear olefines:

| | | |
|---|---|---|
| Butene 1/Butene 2 trans | = | 3.55 |
| Butene 1/Butene 2 cis | = | 95.11 | was reacted on Amberlyst 15 at a LHSV of 5 and at a temperature of 60°C forming a product whose composition was the following one:

| | |
|---|---|
| MTBE | 5.41% by weight |
| methanol | 0.43% by weight |
| isobutene | 0.76% by weight |
| butene 1 | 52.25% by weight |
| butene 2 trans | 15.88% by weight |
| butene 2 cis | 0.66% by weight |
| other $C_4$ hydrocarbons | 27.60% by weight |
| $C_8$ olefines | traces | and in which the ratio between the linear olefines was the following:

| | | |
|---|---|---|
| Butene 1/Butene 2 trans | = | 3.29 |
| Butene 1/Butene 2 cis | = | 79.17 |

EXAMPLE 6

A stream to the secondary reactor different from the foregoing ones having as composition:

| | |
|---|---|
| MTBE | 3.77% by weight |
| methanol | 4.55% by weight |
| isobutene | 2.03% by weight |
| butene 1 | 54.83% by weight |
| butene 2 trans | 12.91% by weight |
| butene 2 cis | 0.28% by weight |
| other $C_4$ hydrocarbons | 21.63% by weight | in which the molar ratio between isobutene and methanol was 0.255 and in which the linear olefines were distributed according to the following ratios:

| | | |
|---|---|---|
| Butene 1/Butene 2 trans | = | 4.25 |
| Butene 1/Butene 2 cis | = | 195.82 | was reacted on Amberlyst 15 at a LHSV of 5 and at a temperature of 80°C forming a product having the following composition:

| | |
|---|---|
| MTBE | 6.49% by weight |
| methanol | 3.55% by weight |
| isobutene | 0.30% by weight |
| butene 1 | 54.60% by weight |
| butene 2 trans | 13.00% by weight |
| butene 2 cis | 0.40% by weight |
| other $C_4$ hydrocarbons | 21.66% by weight |
| $C_8$ olefines | traces | in which the ratio between the linear olefines was the following one:

| | | |
|---|---|---|
| Butene 1/Butene 2 trans | = | 4.20 |
| Butene 1/Butene 2 cis | = | 136.50 |

What we claim is:

1. In a process of preparing methyl tert-butyl ether by reacting isobutylene with methanol, the improvement which comprises carrying out said reaction in two stages by feeding a hydrocarbon stream containing isobutylene and methanol to a primary reaction zone at a temperature in the range of from 50° to 90°C and at a pressure in the range of from 10 to 30 atmospheres wherein the isobutylene partially reacts with the methanol in the presence of a catalyst consisting of an acid ion exchange resin to form methyl tert-butyl ether, separating said methyl tert-butyl ether by distillation from the residue of isobutylene and methanol and all other hydrocarbons in the feed stream, feeding said residue and other hydrocarbons to a secondary reaction zone where the residue of isobutylene and methanol are caused to react in the liquid phase in the temperature range of from 60° to 100°C and in the pressure range of from 15 to 40 atmospheres in the presence of a catalyst consisting of an acid ion exchange resin to form additional methyl tert-butyl ether, and then recovering said additional methyl tert-butyl ether by distillation to leave a balance of said other hydrocarbons practically free from isobutylene.

2. A process as claimed in claim 1, wherein said hydrocarbon stream containing isobutylene is a $C_4$ olefinic stream.

* * * * *

UNITED STATES PATENT AND TRADEMARK OFFICE
CERTIFICATE OF CORRECTION

PATENT NO. : 3,979,461
DATED     : September 7, 1976
INVENTOR(S) : Francesco Ancillotti, Gianni Oriani and Ermanno Pescarollo It is certified that error appears in the above—identified patent and that said Letters Patent are hereby corrected as shown below:

Page 1, [73], Correct the line to read --[73] Assignee:

Snamprogetti S.p.A., San Donato Milanese, Italy--

Column 1, Line 67, After the comma ",", correct "a" to read

--and a--

Column 2, line 25, Correct "C4" to read --$C_4$-- line 28, Correct "4" to read --4--

Signed and Sealed this

Seventh Day of June 1977

[SEAL]

Attest:

RUTH C. MASON
*Attesting Officer*

C. MARSHALL DANN
*Commissioner of Patents and Trademarks*